(12) United States Patent
Tamura et al.

(10) Patent No.: US 9,464,039 B2
(45) Date of Patent: Oct. 11, 2016

(54) METHOD FOR PRODUCING UNSATURATED NITRILE

(75) Inventors: Sho Tamura, Tokyo (JP); Sadao Shoji, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 219 days.

(21) Appl. No.: 13/994,230

(22) PCT Filed: Oct. 13, 2011

(86) PCT No.: PCT/JP2011/073576
§ 371 (c)(1),
(2), (4) Date: Jun. 14, 2013

(87) PCT Pub. No.: WO2012/117605
PCT Pub. Date: Sep. 7, 2012

(65) Prior Publication Data
US 2013/0274500 A1 Oct. 17, 2013

(30) Foreign Application Priority Data
Mar. 2, 2011 (JP) .................................. 2011-045358

(51) Int. Cl.
| | |
|---|---|
| C07C 253/24 | (2006.01) |
| B01J 23/30 | (2006.01) |
| B01J 23/00 | (2006.01) |
| B01J 23/28 | (2006.01) |
| B01J 27/057 | (2006.01) |

(52) U.S. Cl.
CPC ............ *C07C 253/24* (2013.01); *B01J 23/002* (2013.01); *B01J 23/28* (2013.01); *B01J 23/30* (2013.01); *B01J 27/0576* (2013.01); *B01J 2523/00* (2013.01)

(58) Field of Classification Search
None
See application file for complete search history.

(56) References Cited

U.S. PATENT DOCUMENTS

| | | | |
|---|---|---|---|
| 5,049,692 A | 9/1991 | Hatano et al. | |
| 5,380,933 A | 1/1995 | Ushikubo et al. | |
| 5,472,925 A | 12/1995 | Ushikubo et al. | |
| 5,907,052 A | 5/1999 | Hamada et al. | |
| 6,043,186 A | 3/2000 | Komada et al. | |
| 6,063,728 A | 5/2000 | Hinago et al. | |
| 8,772,195 B2* | 7/2014 | Ishii et al. | ......... 502/246 |
| 2002/0115879 A1* | 8/2002 | Hinago et al. | ......... 558/323 |

FOREIGN PATENT DOCUMENTS

| | | |
|---|---|---|
| EP | 2 570 186 A1 | 3/2013 |
| JP | 2-257 A | 1/1990 |
| JP | 5-208136 A | 8/1993 |
| JP | 5-279313 A | 10/1993 |
| JP | 10-28862 A | 2/1998 |
| JP | 11-124361 A | 5/1999 |
| JP | 2001-213855 A | 8/2001 |
| JP | 2007-308423 A | 11/2007 |
| WO | WO 2009/048533 A2 | 4/2009 |
| WO | WO 2009/048553 A2 | 4/2009 |
| WO | WO 2009/151254 A2 | 12/2009 |
| WO | WO2009151254 * | 12/2009 |
| WO | WO2010/087262 * | 8/2010 |

OTHER PUBLICATIONS

Grasselli et al., "Doping of MoVNbTeO (M1) and MoVTeO (M2) Phases for Selective Oxidation of Propane and Propylene to Acrylic Acid", Top Catal, vol. 50, 2008, pp. 66-73.
European Search Report, dated Feb. 28, 2014, for European Application No. 11859889.5.

* cited by examiner

*Primary Examiner* — Rebecca Anderson
*Assistant Examiner* — Po-Chih Chen
(74) *Attorney, Agent, or Firm* — Birch, Stewart, Kolasch & Birch, LLP

(57) ABSTRACT

A method for producing an unsaturated nitrile by subjecting propane to a vapor-phase catalytic ammoxidation reaction using a fluidized bed reactor in the presence of a composite oxide catalyst containing Mo, V, and Nb, the method comprising the step of: adding a tungsten compound into the fluidized bed reactor to adjust a molar ratio (W/Mo ratio) of tungsten contained in a tungsten compound to molybdenum contained in the composite oxide catalyst that exist within the fluidized bed reactor so that the molar ratio is in the range of 0.0001 to 0.1.

3 Claims, No Drawings

METHOD FOR PRODUCING UNSATURATED NITRILE

BACKGROUND OF THE INVENTION

1. Field of the Invention

The present invention relates to a method for subjecting propane to a vapor-phase catalytic ammoxidation reaction to produce a corresponding unsaturated nitrile.

2. Description of the Related Art

It is conventionally known that a method for subjecting propylene to a vapor-phase catalytic ammoxidation reaction to produce a corresponding unsaturated nitrile. In recent years, attention has been directed to a method for subjecting propane instead of propylene to a vapor-phase catalytic ammoxidation reaction to produce a corresponding unsaturated nitrile.

Hitherto, in subjecting propane to a vapor-phase catalytic ammoxidation to produce a corresponding unsaturated nitrile, various techniques have been examined, for example, a technique for adding a molybdenum compound into a reactor during the reaction to maintain the yield of a target product, or a technique for again impregnation with, calcination of, and drying of a catalyst to restore the yield of a target product if the catalyst is deactivated by the reaction.

For example, Patent Literature 1 discloses a technique for adding a molybdenum compound during a vapor-phase catalytic ammoxidation reaction using a Mo—V—Sb—Nb-based catalyst.

Moreover, Patent Literature 2 describes a method for mixing a composite oxide catalyst with an additive such as an antimony compound, a molybdenum compound, a tellurium compound, and a tungsten compound, and subjecting the obtained catalyst to a reaction.

Further, Patent Literature 3 describes a method for impregnating a Mo—V—Sb/Te-based catalyst with a solution containing one or more elements selected from the group consisting of tungsten, molybdenum, chromium, zirconium, titanium, niobium, tantalum, vanadium, boron, bismuth, tellurium, palladium, cobalt, nickel, iron, phosphor, silicon, rare-earth elements, alkali metals, and alkali earth metals.

Patent Literature 1: Japanese Patent Laid-Open No. 2007-308423
Patent Literature 2: International Publication WO 2009-048553
Patent Literature 3: Japanese Patent Laid-Open No. 10-28862

According to the examination by the present inventors, however, in the case where a molybdenum compound is added during the ammoxidation reaction as in the method described in Patent Document 1, the performance of the catalyst can be restored to nearly an initial state, but cannot be improved so as to exceed the initial state. Accordingly, the ability of the catalyst is still insufficient.

Moreover, in a method described in Patent Document 2, although the problems are not clear because the document and Examples have no sufficient description of the amount to be added of a tungsten compound, excessive addition of a tungsten compound promotes burning of ammonia in a raw material gas to increase the amount of ammonia to be consumed and to decrease the yield of acrylonitrile.

Further, in a method described in Patent Document 3, a facility for impregnating a solution or the like with a catalyst is needed, and the number of steps is increased. Accordingly, cost is increased and the process is complicated.

In view of the above-mentioned situation, an object of the present invention is to provide a method for producing an unsaturated nitrile in which no complicated steps such as impregnation and drying are needed, and a higher selectivity is provided.

SUMMARY OF THE INVENTION

In order to achieve the object above, as a result of extensive research, the present inventors have found that in conducting a vapor-phase catalytic ammoxidation reaction using a Mo—V—Nb-based composite oxide catalyst, if a proper amount of a tungsten compound is added into a fluidized bed reactor, the selectivity of a target compound is increased.

Namely, the present invention is as follows:

[1] A method for producing an unsaturated nitrile by subjecting propane to a vapor-phase catalytic ammoxidation reaction using a fluidized bed reactor in the presence of a composite oxide catalyst containing Mo, V, and Nb, the method comprising the step of:

adding a tungsten compound into the fluidized bed reactor to adjust a molar ratio (W/Mo ratio) of tungsten contained in the tungsten compound to molybdenum contained in the composite oxide catalyst that exist within the fluidized bed reactor so that the molar ration is in the range of 0.0001 to 0.1.

[2] The method for producing an unsaturated nitrile according to [1], comprising the step of adding a molybdenum compound into the fluidized bed reactor.

[3] The method for producing an unsaturated nitrile according to [1] or [2] above, wherein the composite oxide catalyst comprises a composite oxide represented by the following composition formula (1):

$$Mo_1V_aNb_bA_cX_dZ_eO_n \qquad (1)$$

wherein component A represents at least one or more elements selected from Te and Sb; component X represents at least one or more elements selected from W, Bi, and Mn; component Z represents at least one or more elements selected from La, Ce, Pr, Yb, Y, Sc, Sr, and Ba; a, b, c, d, e, and n each represent an atomic ratio of the corresponding element per Mo atom; a is in the range of $0.01 \leq a \leq 1$; b is in the range of $0.01 \leq b \leq 1$; c is in the range of $0.01 \leq c \leq 1$; d is in the range of $0 \leq d \leq 1$; e is in the range of $0 \leq e \leq 1$; and n represents a number determined by valences of the component elements.

[4] The method for producing an unsaturated nitrile according to any of [1] to [3] above, wherein the composite oxide is carried on 20 to 70% by mass of silica based on a whole amount of the catalyst in terms of $SiO_2$.

Advantageous Effects of Invention

According to the present invention, a method for producing an unsaturated nitrile that can provide a higher selectivity of a target compound in a simpler manner can be provided.

DETAILED DESCRIPTION OF THE PREFERRED EMBODIMENT

Hereinafter, an embodiment of the present invention (hereinafter, referred to as "the present embodiment") will be described in detail. The present invention is not limited to the following embodiment, and many variations may be made within the scope of the present invention.

The method for producing an unsaturated nitrile according to the present embodiment is a method for producing an unsaturated nitrile by subjecting propane to a vapor-phase catalytic ammoxidation reaction using a fluidized bed reactor in the presence of a composite oxide catalyst containing Mo, V, and Nb, the method comprising the step of adding a tungsten compound into the fluidized bed reactor to adjust a molar ratio (W/Mo ratio) of tungsten contained in the tungsten compound to molybdenum contained in the composite oxide catalyst that exist within the fluidized bed reactor so that the molar ratio is in the range of 0.0001 to 0.1.

[1] Method for Producing Composite Oxide Catalyst (a) Complex Oxide Catalyst

The composite oxide catalyst in the present embodiment comprises a composite oxide containing Mo, V, and Nb. Preferably, the composite oxide is carried on a carrier. The composite oxide catalyst used to produce a corresponding unsaturated nitrile from propane by a vapor-phase catalytic ammoxidation reaction contains Mo, V, and Nb from the viewpoint of demonstration of an effect of improving the selectivity by an interactive effect with a tungsten compound described later.

From the viewpoint of improvement in the yield of the target compound, preferably, the composite oxide catalyst further contains component A (A is at least one or more elements selected from Te and Sb) in addition to Mo, V, and Nb. The composite oxide containing Mo, V, Nb, and component A easily forms a bronze structure having a high crystallinity, and it is thought that the structure advantageously acts on the ability of the catalyst in the ammoxidation reaction of propane, although the reason is not clear.

From the viewpoint of the selectivity of the target product and conducting a long-term fluidized reaction, a more preferable composite oxide catalyst comprises a composite oxide represented by the following composition formula (1):

$$Mo_1V_aNb_bA_cX_dZ_eO_n \qquad (1)$$

wherein component A represents at least one or more elements selected from Te and Sb; component X represents at least one or more elements selected from W, Bi, and Mn; component Z represents at least one or more elements selected from La, Ce, Pr, Yb, Y, Sc, Sr, and Ba; a, b, c, d, e, and n each represent an atomic ratio of the corresponding element per Mo atom; a is in the range of $0.01 \leq a \leq 1$; b is in the range of $0.01 \leq b \leq 1$; c is in the range of $0.01 \leq c \leq 1$; d is in the range of $0 \leq d \leq 1$; e is in the range of $0 \leq e \leq 1$; and n represents the number determined by valences of the component elements.

From the viewpoint of suppressing production of a byproduct and improving the selectivity of the target product, preferably, the atomic ratio a of V per Mo atom is in the range of 0.1 to 0.4, and the atomic ratio b of Nb per Mo atom is in the range of 0.02 to 0.2.

Component A represents at least one or more elements selected from Te and Sb. From the viewpoint of suppressing production of a byproduct and improving the selectivity of the target product, the atomic ratio c of component A per Mo atom is preferably in the range of 0.01 to 0.6, and more preferably in the range of 0.1 to 0.4. In an ordinary industrial method for producing an unsaturated nitrile, the composite oxide catalyst preferably can endure long-term use at a temperature not less than 400° C. In the case where component A is Te, Te is likely to escape during a long-term operation. From the viewpoint, in the industrial method for producing an unsaturated nitrile, component A is preferably Sb.

Moreover, from the viewpoint of suppressing production of a byproduct and improving the selectivity of the target product, in the case where Te is used as component A, the atomic ratio a/c of component A to V is preferably in the range of 1 to 10. In the case where Sb is used as component A, the atomic ratio is preferably in the range of 0.1 to 1.

Component X represents at least one or more elements selected from W, Bi, and Mn. From the viewpoint of suppressing production of a byproduct and improving the selectivity of the target product, the atomic ratio d of component X per Mo atom is $0 \leq d \leq 1$, and preferably satisfies $0.001 \leq d \leq 0.3$. As component X, W, Bi, and Mn are selected from the viewpoint of industrial long-term use. W is particularly preferable because the yield of the target product is likely to be high.

Component Z represents at least one or more elements selected from La, Ce, Pr, Yb, Y, Sc, Sr, and Ba. If component Z is uniformly dispersed within the composite oxide, the effect of improving the yield of target product is likely to be enhanced. As component Z, preferable are at least one or more elements selected from La, Ce, Pr, and Yb. From the viewpoint of the effect of improving the yield of target product, Ce is particularly preferable. Moreover, from the viewpoint of preventing an undesirable reaction by component Z in a slurry as shown in Japanese Patent Laid-Open No. 11-244702, the atomic ratio e of component Z per Mo atom preferably satisfies $0.001 \leq e < 1$, more preferably satisfies $0.001 \leq e < 0.1$, and still more preferably satisfies $0.002 \leq e < 0.01$.

In the composite oxide catalyst in the present embodiment, the composite oxide described above is preferably carried on a carrier. The carrier on which the composite oxide is carried preferably comprises silica as a principal component. In the case where the composite oxide is carried on the carrier comprising silica as the principal component, the composite oxide is likely to have high mechanical strength. Accordingly, the composite oxide is suitable for a vapor-phase catalytic ammoxidation reaction using a fluidized bed reactor. In the case where the carrier comprises silica as the principal component, the content of silica is preferably 20 to 70% by mass, and more preferably 30 to 60% by mass based on the whole amount of the catalyst including the composite oxide and the carrier in terms of $SiO_2$. From the viewpoint of strength and prevention of powdering, the content of silica is preferably not less than 20% by mass based on the whole amount of the catalyst. At a content of silica less than 20% by mass, safe operation is difficult in industrial use of the composite oxide catalyst. Moreover, the lost composite oxide catalyst needs to be replenished, and this case is also economically undesirable. On the other hand, from the viewpoint of providing a sufficient activity to adjust the catalyst at a proper amount, the content of silica is preferably not more than 70% by mass based on the whole amount of the catalyst. In particular, in the case of the fluidized bed, at a content of silica of not more than 70% by mass, the specific gravity of the composite oxide catalyst has a proper value, easily providing a good flow state.

(b) Production of Composite Oxide Catalyst

The composite oxide catalyst in the present embodiment is produced, for example, by the method which includes the following three steps.

(1) the step of preparing raw materials to obtain a raw material-prepared solution;

(2) the step of drying the raw material-prepared solution obtained in the step (1) to obtain a catalyst precursor;

(3) the step of calcining the catalyst precursor obtained in the step (2) to obtain a composite oxide catalyst.

Here, the term "preparing" means to dissolve or disperse raw materials of an element composing the catalyst in a solvent. The solvent is not particularly limited, but water is preferably used.

Moreover, the term "raw material" means a compound containing an element composing the composite oxide catalyst. The raw material is not particularly limited, and, for example, such compounds as described below can be used.

As for raw materials for Mo and V, ammonium heptamolybdate: $[(NH_4)_6Mo_7O_{24}\cdot 4H_2O]$ and ammonium metavanadate: $[NH_4VO_3]$ can appropriately be used, respectively, although the raw materials are not particularly limited.

As raw materials for Nb, niobic acid, an inorganic niobate and an organic niobate can be used. Of these, niobic acid is preferable. Niobic acid is represented by $Nb_2O_5\cdot nH_2O$ and is also referred to as niobium hydroxide or niobium oxide hydrate. Further, a Nb raw material solution in which a molar ratio of dicarboxylic acid/niobium is 1 to 4 is also preferably used. As the dicarboxylic acid, oxalic acid is preferably used.

As raw materials for Sb, diantimony trioxide $[Sb_2O_3]$ is preferable, although not particularly limited.

As raw materials for Te, telluric acid $[H_6TeO_6]$ is preferable, although not particularly limited.

Raw materials for component X are not particularly limited as long as the raw materials contain these elements. A compound containing these elements and a solution in which metal of these elements is solubilized in an appropriate reagent can be used. As the compound containing these elements, an ammonium salt, a nitrate, a carboxylate, an ammonium salt of a carboxylic acid, a peroxocarboxylate, an ammonium salt of a peroxocarboxylic acid, a halogenated ammonium salt, a halide, acetyl acetate, and an alkoxide of these elements can usually be used. Preferably, an aqueous raw material such as a nitrate, and a carboxylate is used.

Raw materials for component Z are not particularly limited as long as the raw materials contain these elements. A compound containing these elements and a solution in which the metal of these elements is solubilized in an appropriate reagent can be used. As the compound containing these elements, a nitrate, a carboxylate, an ammonium salt of a carboxylic acid, a peroxocarboxylate, an ammonium salt of a peroxocarboxylic acid, a halogenated ammonium salt, a halide, acetyl acetate, and an alkoxide of these elements can usually be used. Preferably, an aqueous raw material such as a nitrate, and a carboxylate is used.

Raw materials for silica contained in a carrier are not particularly limited. Silica sol can appropriately be used. However, silica powder can be used either partially or entirely as the silica raw material. The silica powder is preferably produced by a high-temperature method. The silica powder is used with the silica powder previously dispersed in water to facilitate the addition and mixture of the silica powder to a slurry. A dispersing method is not particularly limited. The silica powder can be dispersed by using a general homogenizer, homomixer, and supersonic vibrator or the like either singly or in combination.

Hereinafter, preferred production examples of the composite oxide catalyst including steps (1) to (3) will be described.

(Step (1): Step of Preparing Raw Materials to Obtain Raw Material-Prepared Solution)

In step (1), first, raw materials for Mo, V, component A, component X, component Z, and optionally, a component which becomes any other raw materials are added to water and, then, heated, thereby preparing an aqueous mixed-solution (I). On this occasion, an inside of a container may be in a nitrogen atmosphere. Raw materials for Nb and a dicarboxylic acid are then heated in water while stirring, thereby preparing a mixed-solution (B0). Further, hydrogen peroxide is added to the mixed-solution (B0), thereby preparing an aqueous mixed-solution (II). On this occasion, $H_2O_2/Nb$ (molar ratio) is 0.5 to 20, and preferably 1 to 10.

Depending on a composition to be targeted, the aqueous mixed-solution (I) and the aqueous mixed-solution (II) are appropriately mixed, thereby obtaining an aqueous mixed-solution (III). The obtained aqueous mixed-solution (III) is aged under an air atmosphere, thereby obtaining a slurry raw material-prepared solution.

Aging of the aqueous mixed-solution (III) means to leave standstill or stir the aqueous mixed-solution (III) for a predetermined time. When the composite oxide catalyst is industrially produced, a spray dryer usually has a rate-limiting treatment speed. After a portion of the aqueous mixed-solution (III) is spray-dried, it takes time to complete the spray drying of the whole mixed-solution. In the meantime, the aging of the mixed-solution which is not spray-dried is continued. Therefore, an aging time includes not only an aging time before spray drying but also a time from the start to finish of the spray drying.

The aging time is preferably 90 minutes or more and within 50 hours, and more preferably 90 minutes or more and within 6 hours.

An aging temperature is preferably 25° C. or more from the viewpoint of preventing the condensation of a Mo component and the deposition of V. The aging temperature is preferably 65° C. or less from the viewpoint of preventing the excessive generation of the hydrolysis of a complex containing Nb and hydrogen peroxide and forming a slurry in a preferable form. Therefore, the aging temperature is preferably 25° C. or more and 65° C. or less, and more preferably 30° C. or more and 60° C. or less.

An atmosphere in the container in aging preferably has a sufficient oxygen concentration. Insufficient oxygen may hardly cause substantial change of the aqueous mixed-solution (III). Accordingly, an oxygen concentration of a vapor-phase part in the container is preferably 1 vol % or more. The vapor-phase oxygen concentration can be measured by general methods, for example, using a zirconia type oxygen meter. A place where the vapor-phase oxygen concentration is measured is preferably near an interface between the aqueous mixed-solution (III) and vapor phase. For example, preferably, the vapor-phase oxygen concentration is measured three times at the same point within 1 minute, and the mean value of the three measurement results is used as the vapor-phase oxygen concentration. A dilution gas for reducing the vapor-phase oxygen concentration is not particularly limited. Examples of the dilution gas include nitrogen, helium, argon, carbon dioxide, and steam. Industrially, nitrogen is preferable. As a gas for increasing the vapor-phase oxygen concentration, pure oxygen or air with a high oxygen concentration is preferable.

Some change is considered to occur in an oxidation/reduction state of the component contained in the aqueous mixed-solution (III) by the aging. The occurrence of some change is suggested from the occurrence of change in color and change in an oxidation-reduction potential, or the like of the aqueous mixed-solution (III) during the aging. As a result, the difference in the ability between the composite oxide catalysts occurs, which are obtained by the presence or absence of the aging for 90 minutes or more and within 50 hours in an atmosphere having an oxygen concentration of 1 to 25 vol %. Specifically, it is extremely difficult to correctly identify change in the form of the component in the liquid during the aging. However, catalysts having a different aging time are produced, and the ability is evaluated, and thereby it can be inferred that an aging time imparted to a catalyst having a good ability is preferable and a slurry having some preferable form is formed on this occasion.

It is considered that the oxidation-reduction potential of the aqueous mixed-solution (III) is controlled by a potential (600 mV/AgCl) of an aqueous raw-material solution (II), and that Nb oxalate peroxide contained and other metal components in the aqueous raw-material solution (II) cause some oxidation-reduction reaction to cause temporal reduction in the potential. The oxidation-reduction potential is preferably 450 to 530 mV/AgCl, and more preferably 470 to 510 mV/AgCl.

The oxygen concentration during the aging is preferably 1 vol % or more from the viewpoint of preventing excessive delay in the progress of the oxidation-reduction reaction having an influence on some change in the oxidation/reduction state of the components contained in the aqueous mixed-solution (III), and preventing some excessive oxidation of the oxidation/reduction state in the slurry. On the other hand, the oxygen concentration during the aging is preferably 25 vol % or less from the viewpoint of preventing some excessive reduction of the slurry caused by the excessive progress of the oxidation-reduction reaction. Anyhow, it is necessary to maintain the oxygen concentration in an appropriate range since vapor-phase oxygen has an influence on the oxidation-reduction condition of the slurry. The range of the oxygen concentration is more preferably 5 to 23 vol %, and still more preferably 10 to 20 vol %.

During aging, moisture content may be vaporized to produce condensation. If aging is performed in an open system, the moisture content is naturally vaporized. If aging is performed under an atmosphere of a concentration of oxygen of 1 to 25 vol %, the ability of the catalyst is likely to be further improved.

When the composite oxide is carried on silica, a raw material-prepared solution containing silica sol is prepared. The silica sol can appropriately be added thereto. An aqueous dispersion of the silica powder can be used as a portion of the silica sol. The aqueous dispersion of such silica powder can also appropriately be added.

When Sb (antimony) is used as component A, hydrogen peroxide is preferably added to the aqueous mixed-solution (I) or a liquid containing components of the aqueous mixed-solution (I) during preparation. On this occasion, $H_2O_2$/Sb (molar ratio) is preferably 0.01 to 5, and more preferably 0.05 to 4. On this occasion, stirring is preferably continued at 30° C. to 70° C. for 30 minutes to 2 hours.

(Step (2): Drying Step)

The drying step is a step of drying the raw material-prepared solution obtained in the step (1) to obtain a catalyst precursor. Here, the "catalyst precursor" refers to a dry powder obtained by drying the raw material-prepared solution, and a powder before calcining. Drying can be performed by known methods such as spray drying or evaporation to dryness. Of these, the spray drying is preferably used to obtain minute spherical catalyst precursor. Spraying in the spray drying method can be performed by a centrifugal system, a two-fluid-nozzle system, or a high-pressure nozzle system. Air heated by steam, and an electric heater or the like can be used as a heat source for drying. An inlet temperature of a dryer of a spray drying device is preferably 150 to 300° C. An outlet temperature of the dryer is preferably 100 to 160° C.

(Step (3): Calcining Step)

The calcining step is a step of calcining the catalyst precursor obtained in the step (2) to obtain a composite oxide catalyst. A rotary kiln can be used as a calcining apparatus. The shape of a calcining device is not particularly limited. When the shape of the calcining device is tubular, continuous calcination can be carried out. The shape of a calcining tube is not particularly limited. However, the shape of the calcining tube is preferably cylindrical. A heating system is preferably an external heating system. An electric furnace can appropriately be used. The size and material or the like of the calcining tube can be suitably selected depending on a calcining condition and a production amount. The inner diameter of the calcining tube is preferably 70 to 2000 mm, and more preferably 100 to 1200 mm. The length of the calcining tube is preferably 200 to 10000 mm, and more preferably 800 to 8000 mm. When an impact is imparted to the calcining device, the thickness of the calcining device is preferably 2 mm or more, and more preferably 4 mm or more from the viewpoint that the calcining device has an enough thickness not to be broken by the impact. The thickness of the calcining device is preferably 100 mm or less, and more preferably 50 mm or less from the viewpoint that the impact is sufficiently transmitted into the calcining device. The material of the calcining tube is not particularly limited as long as the calcining tube has heat resistance and strength not to be broken by the impact. SUS can be appropriately used as the material of the calcining tube.

A weir plate having a central part having a hole through which powder passes is provided vertically to the flow of the powder in the calcining tube, and thereby the calcining tube can be also partitioned into two or more zones. A holding time in the calcining tube is easily secured by disposing the weir plate. The number of the weir plates may be one or more. The material of the weir plate is preferably a metal, and a weir plate made of the same material as that of the calcining tube can appropriately be used. The height of the weir plate can be adjusted in accordance with a holding time which should be secured. For example, when powder is supplied at 250 g/hr using a rotary kiln having a calcining tube having an inner diameter of 150 mm and a length of 1150 mm and made of SUS, the height of the weir plate is preferably 5 to 50 mm, more preferably 10 to 40 mm, and still more preferably 13 to 35 mm. The thickness of the weir plate is not particularly limited, and is preferably adjusted in accordance with the size of the calcining tube. For example, in the case of a rotary kiln having a calcining tube having an inner diameter of 150 mm and a length of 1150 mm and made of SUS, the thickness of the calcining tube is preferably 0.3 mm or more and 30 mm or less, and more preferably 0.5 mm or more and 15 mm or less.

In order to prevent crack and crazing or the like of the catalyst precursor and to uniformly calcine the dry powder, the calcining tube is preferably rotated. The rotation speed of the calcining tube is preferably 0.1 to 30 rpm, more preferably 0.5 to 20 rpm, and still more preferably 1 to 10 rpm.

For the calcination of the catalyst precursor, preferably, the heating temperature of the catalyst precursor is continuously or intermittently raised to a temperature in the range of 550 to 800° C. from a temperature lower than 400° C.

A calcining atmosphere may be under an air atmosphere or under an air flow. However, at least a portion of the calcination is preferably carried out while an inert gas which does not substantially contain oxygen, such as nitrogen, flows. The supplied amount of the inert gas is 50 N liters or more per 1 kg of the catalyst precursor, preferably 50 to 5000 N liters, and more preferably 50 to 3000 N liters (N liter means a liter measured under normal temperature and pressure conditions, that is, at 20° C. and 1 atm). On this occasion, the flows of inert gas and catalyst precursor may be in the form of a counter flow or a parallel flow. However, counter flow contact is preferable in consideration of gas components generated from the catalyst precursor and a trace amount of air entering together with the catalyst precursor.

The calcining step can be carried out in a single stage. However, the calcination preferably includes pre-stage calcination performed in the temperature range of 250 to 400° C. and main calcination performed in the temperature range of 550 to 800° C. The pre-stage calcination and the main calcination may be continuously carried out. The main calcination may be carried out anew once the pre-stage calcination has been completed. The pre-stage calcination and the main calcination may each be divided into several stages.

The pre-stage calcination is performed, preferably under an inert gas flow at a heating temperature of 250° C. to 400° C., and preferably 300° C. to 400° C. The pre-stage calcination is preferably held at a constant temperature within the temperature range of 250° C. to 400° C. However, a temperature may fluctuate within the temperature range of 250° C. to 400° C., or be gradually raised or lowered. The holding time of the heating temperature is preferably 30 minutes or more, and more preferably 3 to 12 hours.

A temperature raising pattern until the pre-stage calcining temperature is reached may be linearly raised, or a temperature may be raised so that an arc of an upward or downward convex is formed.

A mean temperature raising rate during temperature raising until the pre-stage calcining temperature is reached is not particularly limited. However, the mean temperature raising rate is generally about 0.1 to 15° C./min, preferably 0.5 to 5° C./min, and more preferably 1 to 2° C./min.

The main calcination is carried out, preferably under an inert gas flow, at 550 to 800° C., preferably at 580 to 750° C., more preferably at 600 to 720° C., and still more preferably at 620 to 700° C. The main calcination is preferably held at a constant temperature within the temperature range of 620° C. to 700° C. However, a temperature may fluctuate within the temperature range of 620° C. to 700° C., or be gradually raised or lowered. The time of the main calcination is 0.5 to 20 hours, and preferably 1 to 15 hours. When the calcining tube is partitioned with a weir plate, the catalyst precursor and/or a composite oxide catalyst continuously passes through at least 2 zones, preferably 2 to 20 zones, and more preferably 4 to 15 zones. A temperature can be controlled using one or more controllers. However, in order to obtain the desired calcining temperature pattern, a heater and a controller are preferably disposed in each of the zones partitioned with these weir plates to control the temperature. For example, when the seven weir plates are disposed so that a length of portion of the calcining tube entering a heating furnace is equally divided into eight, and the calcining tube partitioned into the eight zones is used, the setting temperature of each of the eight zones is preferably controlled by the heater and the controller disposed in each of the zones so that the temperature of the catalyst precursor and/or the composite oxide catalyst has the desired calcining temperature pattern. An oxidizing component (for example, oxygen) or a reducing component (for example, ammonia) may be added to the calcining atmosphere under the inert gas flow as necessary.

A temperature raising pattern until the main calcining temperature is reached may be linearly raised, or a temperature may be raised so that an arc of an upward or downward convex is formed.

A mean temperature raising rate in temperature raising until the main calcining temperature is reached is not particularly limited. However, the mean temperature raising rate is generally about 0.1 to 15° C./min, preferably 0.5 to 10° C./min, and more preferably 1 to 8° C./rain.

A mean temperature lowering rate after the main calcination is completed is 0.01 to 1000° C./min, preferably 0.05 to 100° C./min, more preferably 0.1 to 50° C./min, and still more preferably 0.5 to 10° C./min. A temperature lower than the main calcining temperature is also preferably held once. A holding temperature is lower than the main calcining temperature by 10° C., preferably 50° C., and more preferably 100° C. A holding time is 0.5 hours or more, preferably 1 hour or more, more preferably 3 hours or more, and still more preferably 10 hours or more.

When the main calcination is carried out anew once the pre-stage calcination has been completed, a low temperature treatment is preferably performed in the main calcination.

A time required for the low temperature treatment, that is, a time required for reducing the temperature of the catalyst precursor and/or the composite oxide catalyst and raising the temperature to the calcining temperature can appropriately be adjusted by the size, the thickness, and the material of the calcining device, a catalyst production amount, a series of periods for continuously calcining the catalyst precursor and/or the composite oxide catalyst, and a fixing rate and a fixing amount, or the like. For example, when a calcining tube having an inner diameter of 500 mm, a length of 4500 mm, and a thickness of 20 mm, and made of SUS is used, the time required for the low temperature treatment is preferably within 30 days during the series of periods for continuously calcining a catalyst, more preferably within 15 days, still more preferably within 3 days, and particularly preferably within 2 days.

For example, when catalyst precursor is supplied at a rate of 35 kg/hr while a rotary kiln having a calcining tube having an inner diameter of 500 mm, a length of 4500 mm, and a thickness of 20 mm and made of SUS is rotated at 6 rpm, and the main calcining temperature is set to 645° C., the step of lowering a temperature to 400° C. and raising the temperature to 645° C. can be performed in about 1 day. When calcination is continuously performed for 1 year, the calcination can be performed by carrying out such low temperature treatment once a month while a temperature of an oxide layer is stably maintained.

[2] Method for Producing Unsaturated Nitrile

In the present embodiment, in the presence of the composite oxide catalyst, using a fluidized bed reactor, propane is subjected to a vapor-phase catalytic ammoxidation reaction, thereby producing a corresponding unsaturated nitrile.

Propane and ammonia are not necessarily highly pure, and industrial-grade gas such as propane containing impurities such as ethane, ethylene, n-butane and isobutane, and ammonia including impurities such as water can be used.

Air, air enriched with oxygen or pure oxygen can be used as a supply oxygen source. Further, as a dilution gas, helium, argon, carbon dioxide, steam, and nitrogen or the like may be supplied.

A vapor-phase catalytic ammoxidation of propane can be performed under the following conditions.

A molar ratio of oxygen to be supplied for the reaction to propane is 0.1 to 6, and preferably 0.5 to 4.

A molar ratio of ammonia to be supplied for the reaction to propane is 0.3 to 1.5, and preferably 0.7 to 1.2.

A reaction temperature is 350 to 500° C., and preferably 380 to 470° C.

A reaction pressure is $5\times10^4$ to $5\times10^5$ Pa, and preferably $1\times10^5$ to $3\times10^5$ Pa.

A contact time is 0.1 to 10 (sec·g/cc), and preferably 0.5 to 5 (sec·g/cc).

Here, the contact time is expressed by the following formula.

$$\text{Contact time (sec·g/cc)} = (W/F)\times 273/(273+T)\times (0.1013+P)/0.1013\times 60$$

In the formula, W, F and T are defined as follows:
W=Amount (g) of catalyst packed
F=Flow rate (Ncc/sec) of raw material mixed gas under normal conditions (0° C., $1.013\times10^5$ Pa)
T=Reaction temperature (° C.)
P=Reaction pressure (MPa)

As a reaction method in production of an unsaturated nitrile, usually, the conventional method such as a fixed bed method, a fluidized bed method, and a moving bed method can be used. In the production method according to the present embodiment, the fluidized bed reaction is selected from the viewpoint of adding a tungsten compound into the reactor and improving the selectivity of a target compound by an interaction with the composite oxide catalyst. Another merit of the fluidized bed reaction is easy removal of the heat of reaction.

The vapor-phase catalytic ammoxidation reaction may either be a single current system or a recycle system.

[3] Method for Adding Tungsten Compound

The composite oxide catalyst has the catalyst activity as it is. If a tungsten compound is contacted with the composite oxide catalyst during the vapor-phase catalytic ammoxidation reaction using a fluidized bed reactor, the selectivity of the target compound can be improved. For example, even if the selectivity of the target compound is insufficient in the state where a raw material gas and the like are fed to the reactor in which the composite oxide catalyst is placed and the vapor-phase catalytic ammoxidation reaction is advanced, the tungsten compound is added while the reaction is advanced. Thereby, the selectivity can be improved from the initial state.

In the production method according to the present embodiment, in the step of adding a tungsten compound into the fluidized bed reactor, an amount of the tungsten compound is added so that the molar ratio (W/Mo ratio) of tungsten contained in the tungsten compound to molybdenum contained in the composite oxide catalyst is 0.0001 to 0.1 within the fluidized bed reactor. At a W/Mo ratio of not less than 0.0001 within the fluidized bed reactor, the contact frequency of the composite oxide catalyst with the tungsten compound can be increased to efficiently exchange a metal such as molybdenum in the composite oxide catalyst and tungsten. On the other hand, at a W/Mo ratio of not more than 0.1, excessive burning of ammonia can be suppressed, and reduction in the yield of the unsaturated nitrile can be suppressed.

As described above, tungsten may be contained as an element that composes the composite oxide catalyst. Even in that case, addition of the tungsten compound into the fluidized bed reactor can improve the selectivity of the target compound. The present inventors presume that this is because the tungsten compound added into the reactor is related to reforming in the vicinity of the surface of the composite oxide catalyst, and acts differently from the tungsten component mixed into the crystals of the composite oxide catalyst.

More specifically, it is presumed: if the tungsten compound is added into the fluidized bed reactor, the composite oxide catalyst contacts with the tungsten compound, the tungsten compound is diffused by a solid phase reaction on the surface of the composite oxide in the catalyst, and the exchange reaction of tungsten and a metal element such as Mo occurs. The present inventors think that the exchange reaction contributes to improvement in the selectivity of the target compound.

A method for adjusting the molar ratio (W/Mo ratio) of tungsten contained in the tungsten compound to molybdenum contained in the composite oxide catalyst within the fluidized bed reactor at 0.0001 to 0.1 is not particularly limited. As described above, tungsten in the tungsten compound is reduced by the exchange reaction with the metal in the composite oxide. Accordingly, the tungsten compound is preferably replenished so as to avoid the W/Mo ratio less than 0.0001 and the W/Mo ratio more than 0.1. The frequency of replenishment and the amount of the tungsten compound to be replenished one time can be properly set as long as the W/Mo ratio is kept at 0.0001 to 0.1. The molar ratio (W/Mo ratio) of tungsten contained in the tungsten compound to molybdenum contained in the composite oxide catalyst can be determined by the method described later.

Because molybdenum in the catalyst escapes from the reactor during the reaction, the content of molybdenum in the composite oxide catalyst is likely to reduce. In the case where it is desired to keep the amount of tungsten contained in the tungsten compound in the reactor constant, a molybdenum compound is preferably added into the reactor because the W/Mo ratio is increased as the content of molybdenum in the composite oxide catalyst is reduced. Addition of the molybdenum compound leads to increase in the amount of molybdenum within the reactor, but the amount of molybdenum in the composite oxide catalyst is not directly increased. However, if the molybdenum compound exists within the reactor, the molybdenum compound is likely to be taken into the composite oxide catalyst to gradually increase the amount of molybdenum in the composite oxide catalyst as the time passes.

The amount of the molybdenum compound to be added into the reactor is not particularly limited as long as the W/Mo ratio is kept in the range of 0.0001 to 0.1. The amount of the molybdenum compound to be added is preferably 0.01 to 2 g, and more preferably 0.02 to 1.5 g based on 1 kg of the catalyst per day in terms of Mo. If the molybdenum compound is added by the amount in the range above, an amount of molybdenum equivalent to the amount of molybdenum escaping from the catalyst is fed to the reactor. Thereby, the amount of molybdenum in the catalyst is kept to easily prevent reduction in the yield. Moreover, if more than 2 g of molybdenum compound based on 1 kg of the catalyst per day in terms of Mo is added, ammonia in the reaction gas burns due to an excessive amount of the molybdenum compound and decomposed products thereof, and ammonia is likely to be wasted. Moreover, the temperature within the reactor is likely to be raised, leading to an unstable reaction temperature or the like.

Ordinary molybdenum compounds may be added into the reactor, and examples thereof include ammonium heptamolybdate $[(NH_4)_6Mo_7O_{24}\cdot4H_2O]$, molybdenum trioxide $[MoO_3]$, phosphorus molybdate $[H_3PMo_{12}O_{40}]$, silicon molybdate $[H_4SiMo_{12}O_{40}]$, and molybdenum pentachloride

[MoCl$_5$]. Among these, preferable is ammonium heptamolybdate [(NH$_4$)$_6$Mo$_7$O$_{24}$·4H$_2$O] because it is easily decomposed after addition to be taken into the catalyst. Moreover, ammonium heptamolybdate has a small influence to the catalyst due to counter ions of molybdenum in the molybdenum compound, and an effect of maintaining the yield can be easily obtained. A method for adding the molybdenum compound into the reactor is not particularly limited, and the same method for adding the tungsten compound can be used. The molybdenum compound and the tungsten compound can be added separately as long as the W/Mo ratio can be kept. These compounds may be added simultaneously, or may be added at a different timing.

In the case where the molybdenum compound is added during the reaction, the method for adding molybdenum compound may be either of continuous addition and intermittent addition as long as the W/Mo ratio within the reactor is kept at 0.0001 to 0.1. Here, the continuous addition refers to a method for continuously adding molybdenum every day, and the intermittent addition refers to a method for adding molybdenum every several days.

Preferably, a small amount of the tungsten compound is added into the reactor each several days from the viewpoint of suppressing excessive burning of ammonia at the time of addition and preventing large reduction in the yield of the unsaturated nitrile. Examples of a detailed method for adding the tungsten compound include the following two methods (1) and (2), and the method (2) can be further classified into the continuous addition and the intermittent addition:

(1) a method for adding the tungsten compound into the fluidized bed reactor before the vapor-phase catalytic ammoxidation reaction; and (2) a method for adding the tungsten compound into the fluidized bed reactor during the vapor-phase catalytic ammoxidation reaction (continuous addition and intermittent addition).

(Method (1): Method for Adding Tungsten Compound Before Reaction)

In the present embodiment, as the "tungsten compound", a salt of tungsten such as an ammonium salt, a nitrate, a carboxylate, an ammonium salt of a carboxylic acid, a peroxocarboxylate, an ammonium salt of a peroxocarboxylic acid, a halogenated ammonium salt, a halide, acetyl acetate, an alkoxide, a triphenyl compound, a polyoxometalate, and an ammonium salt of a polyoxometalate of tungsten; and a powder raw material such as tungsten trioxide, tungsten dioxide, tungstate, ammonium metatungstate, tungstosilicic acid, silicotungstomolybdic acid, and vanadotungstosilicic acid can be used. Of these, tungsten trioxide and ammonium metatungstate can appropriately be used from the viewpoint that the tungsten compounds have a small influence to the target compound.

Other than the substances above, a composite oxide catalyst having a higher concentration of tungsten than that in the composite oxide catalyst filling the reactor may function as the "tungsten compound" in the present embodiment.

If an excessively large amount of the tungsten compound is added into the reactor, a large amount of ammonia in the raw material gas is likely to burn to reduce the yield of acrylonitrile. If an excessively small amount of the tungsten compound is added into the reactor, the tungsten compound may not be exchanged with a metal such as molybdenum in the composite oxide catalyst within the reactor. Accordingly, an amount of the tungsten compound is added so that the W/Mo ratio within the reactor is in the range of 0.0001 to 0.1, preferably in the range of 0.0002 to 0.08, and more preferably in the range of 0.0005 to 0.05.

The average particle size of the tungsten compound is preferably not more than 500 μm from the viewpoint of preventing the tungsten compound from stagnating in the bottom of the reactor for efficient contact with the catalyst, and is preferably not less than 1 μm from the viewpoint of preventing the tungsten compound from being blown away from the reactor to the outside. The average particle size of the tungsten compound is more preferably 5 to 300 μm, still more preferably 10 to 250 μm, and particularly preferably 20 to 150 μm.

Here, the average particle size of the tungsten compound designates a value obtained by measuring the tungsten compound calcined at 300 to 600° C. for 3 to 5 hours by a particle size measuring apparatus (LS230 made by BECKMAN COULTER, Inc.).

A method for adding the tungsten compound into the reactor is not particularly limited, and the tungsten compound can be fed under pressure from a hopper outside of the reactor via a piping to a dense catalyst layer in the fluidized bed reactor. In this case, as the gas used for feeding the tungsten compound under pressure, air, an inert gas, and the like are used.

(Method (2): Method for Adding Tungsten Compound During Reaction)

The same tungsten compound as in the case of the method (1) can be used.

In the case of the method (2), for the same reason as above, an amount of the tungsten compound is added so that the W/Mo ratio is in the range of 0.0001 to 0.1, preferably in the range of 0.0002 to 0.08, and more preferably in the range of 0.0005 to 0.05.

The same method for adding tungsten compound into the reactor as that above can be used. The tungsten compound may be added alone, or may be mixed with the composite oxide catalyst and the molybdenum compound and added.

In the case where the tungsten compound is added during the reaction, the method for addition may be either of the continuous addition or the intermittent addition as long as the W/Mo ratio within the reactor is kept at 0.0001 to 0.1.

In order to determine the molar ratio (W/Mo ratio) of tungsten contained in the tungsten compound to molybdenum contained in the composite oxide catalyst within the fluidized bed reactor, the number of moles of molybdenum contained in the composite oxide catalyst and the number of moles of tungsten contained in the tungsten compound need to be determined during the reaction.

The concentration of molybdenum in the composite oxide catalyst can be determined as follows: part of the composite oxide catalyst is extracted from the reactor and determined by fluorescent X-ray analysis (X1000 LINT2500). The composite oxide catalyst extracted from the reactor is mixed with the tungsten compound added into the reactor. Accordingly, an accurate concentration of molybdenum cannot be determined if the extracted composite oxide catalyst is measured as it is. In order to determine an accurate concentration of molybdenum in the composite oxide catalyst, examples of the methods include a method in which the particle size of the tungsten compound to be added is made different from the particle size of the composite oxide catalyst filling the reactor in advance; the extracted composite oxide catalyst is sieved out at a predetermined particle size and separated from the tungsten compound, and measured. The number of moles of molybdenum contained in the composite oxide catalyst within the reactor can be determined as follows: the composite oxide catalyst separated from the tungsten compound is subjected to fluorescent X-ray analysis to determine the concentration of molybdenum in the composite oxide catalyst, and the obtained concentration of molybdenum is multiplied by the mass of the composite oxide catalyst. The composite oxide catalyst scatters during the reaction and the mass thereof is reduced. Accordingly, the rate of reduction in the mass is studied in advance, and is expressed as a calibration curve. The mass of the composite oxide catalyst is properly estimated according to the calibration curve. Even for creation of such a calibration curve, the method above is effective in which the particle size of the tungsten compound and the particle size of the composite oxide catalyst different from each other are provided; the tungsten compound is sieved out from the composite oxide catalyst; and the mass ratio is studied. After the rate of reduction in the mass of the composite oxide catalyst is known, the mass of the composite oxide catalyst can be estimated without sieving. Accordingly, it is unnecessary to provide the particle size of the tungsten compound and the particle size of the composite oxide catalyst different from each other for this purpose.

Examples of a method for determining the number of moles of tungsten contained in the tungsten compound include: (1) a method in which part of the composite oxide catalyst is extracted from the reactor; the concentration of tungsten taken into the composite oxide catalyst is determined by the fluorescent X-ray analysis; the concentration of tungsten is multiplied by the composite oxide catalyst to calculate the number of moles of the tungsten compound taken in; the number of moles of the tungsten compound taken in is subtracted from the number of moles of the tungsten compound added into the reactor, and (2) a method in which in the case where the same composite oxide catalyst is used to conduct the reaction, the calibration curve of the amount of tungsten to be taken in is created in advance from the amount of the tungsten compound to be added and the number of days for the reaction; according to the calibration curve, the amount of tungsten contained in the tungsten compound within the reactor is determined by calculation.

EXAMPLES

Hereinafter, the present embodiment will be further described in detail with reference to examples and comparative examples. However, the range of the present embodiment is not limited to the examples.

In the examples and the comparative examples, the conversion of propane, selectivity of acrylonitrile, and yield of acrylonitrile respectively follow the following definitions.

conversion of propane (PN) (%)=(Number of moles of reacted propane)/(Number of moles of supplied propane)×100

Selectivity of Acrylonitrile (AN) (%)=(Number of moles of produced acrylonitrile)/(Number of moles of reacted propane)×100

Yield of Acrylonitrile (AN) (%)=(Number of moles of produced acrylonitrile)/(Number of moles of supplied propane)×100

(Preparation of Niobium Mixed-Solution)

A niobium mixed-solution was prepared by a method as described below.

To 10 kg of water, 0.956 kg of niobic acid containing 80.0% by mass of niobium in terms of $Nb_2O_5$ and 3.291 kg of oxalic acid dihydrate [$H_2C_2O_4 \cdot 2H_2O$] were added. A molar ratio of oxalic acid/niobium as feedstocks was 5.0 and a concentration of feedstock niobium was 0.50 (mol-Nb/kg-solution). The resultant solution was heated for two hours at 95° C. with stirring, thereby obtaining a mixed-solution in which niobium was dissolved. This mixed-solution was left standstill, cooled with ice, subjected to a suction filtration for removing a solid content, thereby obtaining a uniform niobium mixed-solution. The molar ratio of the oxalic acid/niobium of this niobium mixed-solution was 2.75 by the analysis described below.

10 g of this niobium mixed-solution was precisely weighed and put in a crucible, dried for a night at 95° C., and subjected to a heat treatment for one hour at 600° C., thereby obtaining 0.760 g of $Nb_2O_5$. From this result, the niobium concentration was 0.572 (mol-Nb/kg-solution).

3 g of this niobium mixed-solution was precisely weighed and put in a glass beaker having a capacity of 300 ml, added with 200 ml of hot water having a temperature of about 80° C. and, then, added with 10 ml of a 1:1 sulfuric acid. The resultant mixed-solution was titrated by using a 1/4 N $KMnO_4$ solution with stirring while being kept at a temperature of 70° C. on a hot stirrer. A point at which a faint light pink color by $KMnO_4$ lasted for about 30 seconds or more was defined as an end-point. A concentration of oxalic acid was determined on the basis of the resultant titer in accordance with the following formula and, as a result, it was 1.570 (mol-oxalic acid/kg).

$$2KMnO_4+3H_2SO_4+5H_2C_2O_4 \rightarrow K_2SO_4+2MnSO_4+10CO_2+8H_2O$$

The obtained niobium mixed-solution was used as a niobium mixed-solution ($B_0$) for use in preparation of a catalyst to be described below.

Example 1

Preparation of Composite Oxide Catalyst

A composite oxide catalyst having a feedstock composition formula represented by 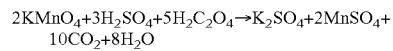
50.0 wt %-$SiO_2$ was produced as follows.

To 1683 g of water, 411.3 g of ammonium heptamolybdate [$(NH_4)_6Mo_7O_{24} \cdot 4H_2O$], 54.1 g of ammonium metavanadate [$NH_4VO_3$], and 67.8 g of diantimony trioxide [$Sb_2O_3$] were added and heated for 1 hour at 95° C. with stirring, thereby obtaining an aqueous raw-material solution (I).

To 404.4 g of a niobium mixed-solution ($B_0$), 66.3 g of a hydrogen peroxide solution containing 30 wt % of $H_2O_2$ was added and mixed for 10 minutes at room temperature with stirring, thereby preparing an aqueous raw-material solution (II).

After the obtained aqueous raw-material solution (I) was cooled to 70° C., 735.7 g of silica sol containing 34.0 wt % of $SiO_2$ was added thereto and, further, 129.3 g of a hydrogen peroxide solution containing 30 wt % of $H_2O_2$ was added thereto and then, the resultant mixture was continuously stirred for 30 minutes at 55° C. Next, the aqueous raw-material solution (II), 53.4 g of an aqueous solution of ammonium metatungstate containing 50 wt % of $WO_3$, and a dispersion liquid in which 250 g of silica powder was dispersed in 3375 g of water were sequentially added thereto, thereby obtaining an aqueous mixed-solution (III). The aqueous mixed-solution (III) was aged at 50° C. for 2 hours and 30 minutes after the aqueous raw-material solution (II) was added, thereby obtaining a slurry raw material-prepared solution.

The obtained raw material-prepared solution was supplied to a centrifugal spray dryer and dried, thereby obtaining a microspherical catalyst precursor. Temperatures at an inlet and an outlet of the dryer were respectively 210° C. and 120° C.

200 g of the obtained catalyst precursor was packed in a calcining tube having a diameter of 3 inches and made of SUS, and then, calcined for 2 hours at 680° C. in a flow of a nitrogen gas at a rate of 5.0 NL/min while the tube was rotated, thereby obtain a composite oxide catalyst. The obtained composite oxide catalyst was sieved out at 50 to 100 μm.

(Preparation of Tungsten Trioxide)

From ammonium metatungstate $[(NH_4)_6H_2W_{12}O_{40}]$, 50% by mass of an aqueous solution of ammonium metatungstate was prepared. The aqueous solution was fed to a centrifugal spray dryer and dried. The dried product was molded into a microspherical shape. The temperature at the inlet of the dryer was 210° C., and the temperature at the outlet thereof was 120° C.

200 g of the microspherical ammonium metatungstate was placed on an evaporating dish. Using a fixed type calcining furnace, the microspherical ammonium metatungstate was calcined under the air at 200° C. for 1 hour, and further calcined at 500° C. for 2 hours. Then, the calcined product was extracted and cooled to obtain tungsten trioxide. The obtained tungsten trioxide was sieved out at 20 to 32 μm.

Tungsten trioxide in Examples and Comparative Examples below was prepared by the same method as above.

(Ammoxidation Reaction of Propane)

A glass fluidized bed reactor having an inner diameter of 1B was filled with a mixture of 40 g of the composite oxide catalyst obtained above and 0.35 g of tungsten trioxide obtained above. A mixed gas in a molar ratio of propane:ammonia:oxygen:helium=1:1:3:18 was fed at a reaction temperature of 440° C. under a reaction pressure of normal pressure, and a contact time of 2.9 (sec·g/cc) to conduct an ammoxidation reaction. On day 5 after the reaction was started, the mixture of the composite oxide catalyst and the tungsten compound was extracted from the reactor, and classified by a 50-1 μm sieve. The composition of the obtained product was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0162. The reaction was continued as it was, and the reaction was conducted for 10 days.

The W/Mo ratio on day 5, W/Mo ratio on day 10 (both of them were calculated by the same measurement and calculation. Hereinafter, the same applies.), and the results of the reaction are shown in Table 1.

Comparative Example 1

Preparation of Composite Oxide Catalyst

A composite oxide catalyst was prepared by the same method as in Example 1.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction for 10 days.

The results of the reaction on day 5 and on day 10 are shown in Table 1.

Example 2

Preparation of Composite Oxide Catalyst

A composite oxide catalyst having a feedstock composition formula represented by $Mo_1V_{0.21}Nb_{0.10}Sb_{0.22}W_{0.04}O_n/$ 50.0 wt %-$SiO_2$ was produced as follows.

To 1757 g of water, 408.4 g of ammonium heptamolybdate $[(NH_4)_6Mo_7O_{24}\cdot 4H_2O]$, 56.5 g of ammonium metavanadate $[NH_4VO_3]$, and 74.0 g of diantimony trioxide $[Sb_2O_3]$ were added and heated for 1 hour at 95° C. with stirring, thereby obtaining an aqueous raw-material solution (I).

To 401.6 g of a niobium mixed-solution ($B_0$), 66.3 g of a hydrogen peroxide solution containing 30 wt % of $H_2O_2$ was added and mixed with stirring for 10 minutes at room temperature, thereby preparing an aqueous raw-material solution (II).

After the obtained aqueous raw-material solution (I) was cooled to 70° C., 735.7 g of silica sol containing 34.0 wt % of $SiO_2$ was added thereto and, further, 129.3 g of a hydrogen peroxide solution containing 30 wt % of $H_2O_2$ was added thereto and then, the resultant mixture was continuously stirred for 30 minutes at 55° C. Next, the aqueous raw-material solution (II), 42.4 g of an aqueous solution of ammonium metatungstate containing 50 wt % of $WO_3$, and a dispersion liquid in which 250 g of silica powder was dispersed in 3375 g of water were sequentially added thereto, thereby obtaining an aqueous mixed-solution (III). The aqueous mixed-solution (III) was aged at 50° C. for 2 hours and 30 minutes after the aqueous raw-material solution (II) was added, thereby obtaining a slurry raw material-prepared solution.

The obtained raw material-prepared solution was supplied to a centrifugal spray dryer and dried, thereby obtaining a microspherical catalyst precursor. Temperatures at an inlet and an outlet of the dryer were respectively 210° C. and 120° C.

200 g of the obtained catalyst precursor was packed in a calcining tube having a diameter of 3 inches and made of SUS, and then, calcined for 2 hours at 680° C. in a flow of a nitrogen gas at a rate of 5.0 NL/min while the tube was rotated, thereby obtain a composite oxide catalyst. The obtained composite oxide catalyst was sieved out at 50 to 100 μm.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. Immediately after the reaction was started, 0.05 g of tungsten trioxide was continuously added to the dense catalyst layer within the reactor via a valve for four days. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0094. The reaction was continued as it was, and the reaction was conducted for 10 days.

The W/Mo ratio on day 5, that on day 10, and results of the reaction are shown in Table 1.

Example 3

Preparation of Composite Oxide Catalyst

A composite oxide catalyst was prepared by the same method as in Example 2.
(Ammoxidation Reaction of Propane)
A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 0.02 g of tungsten trioxide was added to the dense catalyst layer within the reactor via a valve. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0002 and relatively low. Then, 0.1 g of tungsten trioxide was added. The reaction was conducted for 10 days.

The W/Mo ratio on day 5, that on day 10, and results of the reaction are shown in Table 1.

Example 4

Preparation of Composite Oxide Catalyst

A composite oxide catalyst was prepared by the same method as in Example 2.
(Ammoxidation Reaction of Propane)
A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 0.55 g of tungsten trioxide was added to the dense catalyst layer within the reactor via a valve, and 0.55 g of tungsten trioxide was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0945. The reaction was continued as it was, and the reaction was conducted for 10 days.

The W/Mo ratio on day 5, that on day 10, and results of the reaction are shown in Table 1.

Comparative Example 2

Preparation of Composite Oxide Catalyst

A composite oxide catalyst was prepared by the same method as in Example 2.
(Ammoxidation Reaction of Propane)
A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 3.0 g of tungsten trioxide was added to the dense catalyst layer within the reactor via a valve, and 3.0 g of tungsten trioxide was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.2534. The reaction was conducted for 10 days.

The W/Mo ratio on day 5, that on day 10, and results of the reaction are shown in Table 1.

Example 5

Preparation of Composite Oxide Catalyst

A composite oxide catalyst was prepared by the same method as in Example 2.
(Ammoxidation Reaction of Propane)
A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 0.3 g of commercially available ammonium metatungstate in the W/Mo ratio was added to the dense catalyst layer within the reactor via a valve, and 0.3 g of commercially available ammonium metatungstate in the W/Mo ratio was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0021. The reaction was continued as it was, and the reaction was conducted for 10 days.

The W/Mo ratio on day 5, that on day 10, and results of the reaction are shown in Table 1.

Comparative Example 3

Preparation of Composite Oxide Catalyst

A composite oxide catalyst was prepared by the same method as in Example 2.
(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction for 10 days.

The results of the reaction on day 5 and on day 10 are shown in Table 1.

Example 6

Preparation of Composite Oxide Catalyst

A composite oxide catalyst having a feedstock composition formula represented by $Mo_1V_{0.22}Nb_{0.11}Te_{0.2}O_n$ was produced as follows.

To 3806 g of water, 832.1 g of ammonium heptamolybdate $[(NH_4)_6Mo_7O_{24}\cdot 4H_2O]$, 120.5 g of ammonium metavanadate $[NH_4VO_3]$, and 214.9 g of telluric acid $[H_6TeO_6]$ were added. While the mixed solution was stirred, the mixed solution was heated to 60° C. and dissolved. Then, the obtained solution was cooled to 30° C. to obtain an aqueous raw-material solution (I).

To 900.0 g of a niobium mixed solution ($B_0$), 66.3 g of a hydrogen peroxide solution containing 30 wt % of $H_2O_2$ was added. The solution was stirred and mixed at room temperature for 10 minutes to prepare an aqueous raw-material solution (II).

The obtained aqueous raw-material solution (I) was sprayed on a Teflon-coated iron plate heated to 140° C. to obtain a microspherical catalyst precursor.

A calcining tube made of SUS and having a diameter of 3 inches was filled with 200 g of the obtained catalyst precursor. Under a flow of nitrogen gas at 5.0 NL/min, while the calcining tube was rotated, the catalyst precursor was calcined at 680° C. for 2 hours to obtain a composite oxide catalyst. The obtained composite oxide catalyst was sieved out at 50 to 100 μm.
(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 0.2 g of tungsten trioxide was added to the dense catalyst layer within the reactor via a valve, and 0.2 g of tungsten trioxide was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0092. The reaction was continued as it was, and the reaction was conducted for 10 days.

The W/Mo ratio on day 5, that on day 10, and results of the reaction are shown in Table 1.

Comparative Example 4

Preparation of Composite Oxide Catalyst

A composite oxide catalyst was prepared by the same method as in Example 6.
(Ammoxidation Reaction of Propane)

A glass fluidized bed reactor having an inner diameter of 1B was filled with 40 g of the composite oxide catalyst obtained. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction for 10 days.

The results of the reaction on day 5 and on day 10 are shown in Table 1.

Example 7

Preparation of Composite Oxide Catalyst

A composite oxide catalyst having a feedstock composition formula represented by $Mo_1V_{0.20}Nb_{0.10}Sb_{0.23}W_{0.03}O_n$/50.0 wt %-$SiO_2$ was produced as follows.

To 1685 g of water, 411.8 g of ammonium heptamolybdate $[(NH_4)_6Mo_7O_{24}\cdot 4H_2O]$, 54.2 g of ammonium metavanadate $[NH_4VO_3]$, and 78.0 g of diantimony trioxide $[Sb_2O_3]$ was added. While the mixed solution was stirred, the mixed solution was heated at 95° C. for 1 hour to obtain an aqueous raw-material solution (I).

To 404.9 g of a niobium mixed solution ($B_0$), 66.3 g of a hydrogen peroxide solution containing 30 wt % of $H_2O_2$ was added. The solution was stirred and mixed at room temperature for 10 minutes to prepare an aqueous raw-material solution (II).

The obtained aqueous raw-material solution (I) was cooled to 70° C., and 735.7 g of silica sol containing 34.0 wt % of $SiO_2$ was added. Further, 129.3 g of a hydrogen peroxide solution containing 30 wt % of $H_2O_2$ was added, and the obtained solution was continuously stirred at 55° C. for 30 minutes. Next, the aqueous raw-material solution (II), 32.1 g of an aqueous solution of ammonium metatungstate containing 50 wt % of WO$_3$, and a dispersion liquid prepared by dispersing 250 g of powder silica in 3375 g of water were sequentially added to obtain an aqueous mixed solution (III). The aqueous mixed solution (III) was aged at 50° C. for 2 hours 30 minutes after addition of the aqueous raw-material solution (II) to obtain a slurry raw material-prepared solution.

The obtained raw material-prepared solution was fed to the centrifugal spray dryer and dried to obtain a microspherical catalyst precursor. The temperature at the inlet of the dryer was 210° C., and the temperature at the outlet thereof was 120° C.

A calcining tube made of SUS and having a diameter of 3 inches was filled with 200 g of the obtained catalyst precursor. Under a flow of nitrogen gas at 5.0 NL/min, while the calcining tube was rotated, the catalyst precursor was calcined at 680° C. for 2 hours to obtain a composite oxide catalyst. The obtained composite oxide catalyst was sieved out at 50 to 100 μm.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 0.2 g of tungsten trioxide was added to the dense catalyst layer within the reactor via a valve, and 0.2 g of tungsten trioxide was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0155. The reaction was continued as it was, and the reaction was conducted for 10 days.

The W/Mo ratio on day 5, that on day 10, and results of the reaction are shown in Table 1.

Comparative Example 5

Preparation of Composite Oxide Catalyst

A composite oxide catalyst was prepared by the same method as in Example 7.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction for 10 days.

The results of the reaction on day 5 and on day 10 are shown in Table 1.

Example 8

Preparation of Composite Oxide Catalyst

A composite oxide catalyst having a feedstock composition formula represented by $Mo_1V_{0.23}Nb_{0.10}Sb_{0.20}W_{0.04}O_n$/50.0 wt %-SiO$_2$ was produced as follows.

To 1939 g of water, 410.5 g of ammonium heptamolybdate [(NH$_4$)$_6$Mo$_7$O$_{24}$·4H$_2$O], 62.1 g of ammonium metavanadate [NH$_4$VO$_3$], and 67.6 g of diantimony trioxide [Sb$_2$O$_3$] were added. While the mixed solution was stirred, the mixed solution was heated at 95° C. for 1 hour to obtain an aqueous raw-material solution (I).

To 403.6 g of a niobium mixed solution (B$_0$), 66.3 g of a hydrogen peroxide solution containing 30 wt % of H$_2$O$_2$ was added. The solution was stirred and mixed at room temperature for 10 minutes to prepare an aqueous raw-material solution (II).

The obtained aqueous raw-material solution (I) was cooled to 70° C., and 735.7 g of silica sol containing 34.0 wt % of SiO$_2$ was added. Further, 129.3 g of a hydrogen peroxide solution containing 30 wt % of H$_2$O$_2$ was added, and the obtained solution was continuously stirred at 55° C. for 30 minutes. Next, the aqueous raw-material solution (II), 42.7 g of aqueous solution of ammonium metatungstate containing 50 wt % of WO$_3$, and a dispersion liquid prepared by dispersing 250 g of powder silica in 3375 g of water were sequentially added to obtain an aqueous mixed solution (III). The aqueous mixed solution (III) was aged at 50° C. for 2 hours 30 minutes after addition of the aqueous raw-material solution (II) to obtain a slurry raw material-prepared solution.

The obtained raw material-prepared solution was fed to the centrifugal spray dryer and dried to obtain a microspherical catalyst precursor. The temperature at the inlet of the dryer was 210° C., and the temperature at the outlet thereof was 120° C.

A calcining tube made of SUS and having a diameter of 3 inches was filled with 200 g of the obtained catalyst precursor. Under a flow of nitrogen gas at 5.0 NL/min, while the calcining tube was rotated, the catalyst precursor was calcined at 680° C. for 2 hours to obtain a composite oxide catalyst. The obtained composite oxide catalyst was sieved out at 50 to 100 μm.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 0.15 g of tungsten trioxide was added to the dense catalyst layer within the reactor via a valve, and 0.15 g of tungsten trioxide was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0129. The reaction was continued as it was, and the reaction was conducted for 10 days.

The W/Mo ratio on day 5, that on day 10, and results of the reaction are shown in Table 1.

Comparative Example 6

Preparation of Composite Oxide Catalyst

A composite oxide catalyst was prepared by the same method as in Example 8.
(Ammoxidation Reaction of Propane)
A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction for 10 days.

The results of the reaction on day 5 and on day 10 are shown in Table 1.

Example 9

Preparation of Composite Oxide Catalyst

A composite oxide catalyst having a feedstock composition formula represented by $Mo_1V_{0.21}Nb_{0.10}Sb_{0.22}W_{0.05}La_{0.005}O_n/50.0$ wt %-$SiO_2$ was produced as follows.

To 1731 g of water, 402.6 g of ammonium heptamolybdate [$(NH_4)_6Mo_7O_{24}\cdot 4H_2O$], 55.7 g of ammonium metavanadate [$NH_4VO_3$], 73.0 g of diantimony trioxide [$Sb_2O_3$], and 5.0 g of lanthanum nitrate hexahydrate $La(NO_3)_3\cdot 6H_2O$ were added. While the mixed solution was stirred, the mixed solution was heated at 95° C. for 1 hour to obtain an aqueous raw-material solution (I).

To 402.9 g of a niobium mixed solution ($B_0$), 66.3 g of a hydrogen peroxide solution containing 30 wt % of $H_2O_2$ was added. The solution was stirred and mixed at room temperature for 10 minutes to obtain an aqueous raw-material solution (II).

The obtained aqueous raw-material solution (I) was cooled to 70° C., and 735.7 g of silica sol containing 34.0 wt % of $SiO_2$ was added. Further, 129.3 g of a hydrogen peroxide solution containing 30 wt % of $H_2O_2$ was added, and the obtained solution was continuously stirred at 55° C. for 30 minutes. Next, the aqueous raw-material solution (II), 52.3 g of an aqueous solution of ammonium metatungstate containing 50 wt % of $WO_3$, and a dispersion liquid prepared by dispersing 250 g of powder silica in 3375 g of water were sequentially added to obtain an aqueous mixed solution (III). The aqueous mixed solution (III) was aged at 50° C. for 2 hours 30 minutes after addition of the aqueous raw-material solution (II) to obtain a slurry raw material-prepared solution.

The obtained raw material-prepared solution was fed to the centrifugal spray dryer and dried to obtain a microspherical catalyst precursor. The temperature at the inlet of the dryer was 210° C., and the temperature at the outlet thereof was 120° C.

A calcining tube made of SUS and having a diameter of 3 inches was filled with 200 g of the obtained catalyst precursor. Under a flow of nitrogen gas at 5.0 NL/min, while the calcining tube was rotated, the catalyst precursor was calcined at 680° C. for 2 hours to obtain a composite oxide catalyst. The obtained composite oxide catalyst was sieved out at 50 to 100 μm.
(Ammoxidation Reaction of Propane)
A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 0.25 g of tungsten trioxide was added to the dense catalyst layer within the reactor via a valve, and 0.25 g of tungsten trioxide was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0226. The reaction was continued as it was, and the reaction was conducted for 10 days.

The W/Mo ratio on day 5, that on day 10, and results of the reaction are shown in Table 1.

Comparative Example 7

Preparation of Composite Oxide Catalyst

A composite oxide catalyst was prepared by the same method as in Example 9.
(Ammoxidation Reaction of Propane)
A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction for 10 days.

The results of the reaction on day 5 and on day 10 are shown in Table 1.

Example 10

Preparation of Composite Oxide Catalyst

A composite oxide catalyst having a feedstock composition formula represented by $Mo_1V_{0.2}Nb_{0.12}Sb_{0.2}W_{0.03}Ce_{0.005}O_n/25.0$ wt %-$SiO_2$ was produced as follows.

To 2563 g of water, 620.2 g of ammonium heptamolybdate [$(NH_4)_6Mo_7O_{24}\cdot 4H_2O$], 81.7 g of ammonium metavanadate [$NH_4VO_3$], 102.2 g of diantimony trioxide [$Sb_2O_3$], and 7.7 g of cerium nitrate hexahydrate $Ce(NO_3)_3\cdot 6H_2O$. While the mixed solution was stirred, the mixed solution was heated at 95° C. for 1 hour to obtain an aqueous raw-material solution (I).

To 731.8 g of a niobium mixed solution ($B_0$), 66.3 g of a hydrogen peroxide solution containing 30 wt % of $H_2O_2$ was added. The solution was stirred and mixed at room temperature for 10 minutes to prepare an aqueous raw-material solution (II).

The obtained aqueous raw-material solution (I) was cooled to 70° C., and 367.9 g of silica sol containing 34.0 wt % of $SiO_2$ was added. Further, 129.3 g of a hydrogen peroxide solution containing 30 wt % of $H_2O_2$ was added, and the obtained solution was continuously stirred at 55° C. for 30 minutes. Next, the aqueous raw-material solution (II), 48.3 g of an aqueous solution of ammonium metatungstate containing 50 wt % of $WO_3$, and a dispersion liquid prepared by dispersing 125 g of powder silica in 1688 g of water were sequentially added to obtain an aqueous mixed solution (III). The aqueous mixed solution (III) was aged at 50° C. for 2 hours 30 minutes after addition of the aqueous raw-material solution (II) to obtain a slurry raw material-prepared solution.

The obtained raw material-prepared solution was fed to the centrifugal spray dryer and dried to obtain a microspherical catalyst precursor. The temperature at the inlet of the dryer was 210° C., and the temperature at the outlet thereof was 120° C.

A calcining tube made of SUS and having a diameter of 3 inches was filled with 200 g of the obtained catalyst precursor. Under a flow of nitrogen gas at 5.0 NL/min, while the calcining tube was rotated, the catalyst precursor was calcined at 680° C. for 2 hours to obtain a composite oxide catalyst. The obtained composite oxide catalyst was sieved out at 50 to 100 μm.

(Ammoxidation Reaction of Propane)

A glass fluidized bed reactor having an inner diameter of 1B was filled with 40 g of the composite oxide catalyst obtained above. A mixed gas in a molar ratio of propane: ammonia:oxygen:helium=1:1:3:18 was fed to a reaction temperature of 440° C., a reaction pressure of 50 kPa, and a contact time of 2.9 (sec·g/cc) to conduct the ammoxidation reaction. On day 2 after the reaction was started, 0.15 g of tungsten trioxide was added to the dense catalyst layer within the reactor via a valve, and 0.15 g of tungsten trioxide was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0082. The reaction was continued as it was, and the reaction was conducted for 10 days.

The W/Mo ratio on day 5, that on day 10, and results of the reaction are shown in Table 1.

Comparative Example 8

Preparation of Composite Oxide Catalyst

A composite oxide catalyst was prepared by the same method as in Example 10.

(Ammoxidation Reaction of Propane)

A glass fluidized bed reactor having an inner diameter of 1B was filled with 40 g of the composite oxide catalyst obtained above. A mixed gas in a molar ratio of propane: ammonia:oxygen:helium=1:1:3:18 was fed at a reaction temperature of 440° C., a reaction pressure of 50 kPa, and a contact time of 2.9 (sec·g/cc) to conduct the ammoxidation reaction for 10 days.

The results of the reaction on day 5 and on day 10 are shown in Table 1.

Example 11

Ammoxidation Reaction of Propane

After Example 2, the ammoxidation reaction was continued for another 5 days. On day 15 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0077. Then, 0.6 g of ammonium heptamolybdate and 0.12 g of tungsten trioxide were added. The reaction was continued as it was, and the reaction was conducted for 30 days.

The W/Mo ratio on day 15, that on day 30, and results of the reaction are shown in Table 1.

Comparative Example 9

Ammoxidation Reaction of Propane

The reaction was continued for 30 days in the same manner as in Example 11 except that tungsten trioxide was not added.

The results of the reaction on day 15 and on day 30 are shown in Table 1.

Example 12

Preparation of Composite Oxide Catalyst

A composite oxide catalyst having a feedstock composition formula represented by $Mo_1V_{0.2}Nb_{0.10}Sb_{0.2}W_{0.04}O_n$/65.0 wt %-$SiO_2$ was produced as follows.

To 1176 g of water, 291.0 g of ammonium heptamolybdate [$(NH_4)_6Mo_7O_{24} \cdot 4H_2O$], 38.3 g of ammonium metavanadate [$NH_4VO_3$], and 47.9 g of diantimony trioxide [$Sb_2O_3$] were added. While the mixed solution was stirred, the mixed solution was heated at 95° C. for 1 hour to obtain an aqueous raw-material solution (I).

To 286.1 g of a niobium mixed solution ($B_0$), 66.3 g of a hydrogen peroxide solution containing 30 wt % of $H_2O_2$ was added. The solution was stirred and mixed at room temperature for 10 minutes to obtain an aqueous raw-material solution (II).

The obtained aqueous raw-material solution (I) was cooled to 70° C., and 956.4 g of silica sol containing 34.0 wt % of $SiO_2$ was added. Further, 129.3 g of a hydrogen peroxide solution containing 30 wt % of $H_2O_2$ was added, and the obtained solution was continuously stirred at 55° C. for 30 minutes. Next, the aqueous raw-material solution (II), 30.2 g of an aqueous solution of ammonium metatungstate containing 50 wt % of $NO_3$, and a dispersion liquid prepared by dispersing 325 g of powder silica in 4388 g of water were sequentially added to obtain an aqueous mixed solution (III). The aqueous mixed solution (III) was aged at 50° C. for 2 hours 30 minutes after addition of the aqueous raw-material solution (II) to obtain a slurry raw material-prepared solution.

The obtained raw material-prepared solution was fed to the centrifugal spray dryer and dried to obtain a microspherical catalyst precursor. The temperature at the inlet of the dryer was 210° C., and the temperature at the outlet thereof was 120° C.

A calcining tube made of SUS and having a diameter of 3 inches was filled with 200 g of the obtained catalyst precursor. Under a flow of nitrogen gas at 5.0 NL/min, while the calcining tube was rotated, the catalyst precursor was calcined at 680° C. for 2 hours to obtain a composite oxide catalyst. The obtained composite oxide catalyst was sieved out at 50 to 100 μm.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 0.3 g of tungsten trioxide was added to the dense catalyst layer within the reactor via a valve, and 0.3 g of tungsten trioxide was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0274. The reaction was continued as it was, and the reaction was conducted for 10 days.

The W/Mo ratio on day 5, that on day 10, and results of the reaction are shown in Table 1.

Comparative Example 10

Preparation of Composite Oxide Catalyst

A composite oxide catalyst was prepared by the same method as in Example 12.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction for 10 days.

The results of the reaction on day 5 and on day 10 are shown in Table 1.

Example 13

Preparation of Composite Oxide Catalyst

A composite oxide catalyst having a feedstock composition formula represented by $Mo_1V_{0.22}Nb_{0.11}Sb_{0.2}O_n/50.0$ wt %-$SiO_2$ was produced as follows.

To 1933 g of water, 428.0 g of ammonium heptamolybdate [$(NH_4)_6Mo_7O_{24}\cdot 4H_2O$], 62.0 g of ammonium metavanadate [$NH_4VO_3$], and 70.5 g of diantimony trioxide [$Sb_2O_3$] were added. While the mixed solution was stirred, the mixed solution was heated at 95° C. for 1 hour to obtain an aqueous raw-material solution (I).

To 462.9 g of a niobium mixed solution ($B_0$), 66.3 g of a hydrogen peroxide solution containing 30 wt % of $H_2O_2$ was added. The solution was stirred and mixed at room temperature for 10 minutes to prepare an aqueous raw-material solution (II).

The obtained aqueous raw-material solution (I) was cooled to 70° C., and 735.7 g of silica sol containing 34.0 wt % of $SiO_2$ was added. Further, 129.3 g of a hydrogen peroxide solution containing 30 wt % of $H_2O_2$ was added, and the obtained solution was continuously stirred at 55° C. for 30 minutes. Next, the aqueous raw-material solution (II), and a dispersion liquid prepared by dispersing 250 g of powder silica in 3375 g of water were sequentially added to obtain an aqueous mixed solution (III). The aqueous mixed solution (III) was aged at 50° C. for 2 hours 30 minutes after addition of the aqueous raw-material solution (II) to obtain a slurry raw material-prepared solution.

The obtained raw material-prepared solution was fed to the centrifugal spray dryer and dried to obtain a microspherical catalyst precursor. The temperature at the inlet of the dryer was 210° C., and the temperature at the outlet thereof was 120° C.

A calcining tube made of SUS and having a diameter of 3 inches was filled with 200 g of the obtained catalyst precursor. Under a flow of nitrogen gas at 5.0 NL/min, while the calcining tube was rotated, the catalyst precursor was calcined at 680° C. for 2 hours to obtain a composite oxide catalyst. The obtained composite oxide catalyst was sieved out at 50 to 100 μm.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction. On day 2 after the reaction was started, 0.25 g of tungsten trioxide was added to the dense catalyst layer within the reactor via a valve, and 0.25 g of tungsten trioxide was further added on day 4. On day 5 after the reaction was started, a mixture of the composite oxide catalyst and the tungsten compound was extracted from the reactor, and classified by a 50-μm sieve. The composition of the obtained composite oxide catalyst was analyzed to determine the numbers of moles of molybdenum and tungsten in the composite oxide catalyst. Based on the analyzed values, the number of moles of tungsten taken into the catalyst was calculated, and the number of moles of tungsten taken into the composite oxide catalyst was subtracted from the number of moles of tungsten in the tungsten compound added. From the obtained value, the number of moles of tungsten contained in the tungsten compound within the reactor was calculated. The W/Mo ratio was determined, and it was 0.0216. The reaction was continued as it was, and the reaction was conducted for 10 days.

The W/Mo ratio on day 5, that on day 10, and results of the reaction are shown in Table 1.

Comparative Example 11

Preparation of Composite Oxide Catalyst

A composite oxide catalyst was prepared by the same method as in Example 13.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of 50 kPa, and a contact time of 2.9 (sec·g/cc) to conduct the ammoxidation reaction for 10 days.

The results of the reaction on day 5 and on day 10 are shown in Table 1.

Example 14

Preparation of Composite Oxide Catalyst

A composite oxide catalyst having a feedstock composition formula represented by $Mo_1V_{0.21}Nb_{0.10}Sb_{0.22}W_{0.03}O_n$/50.0 wt %-$SiO_2$ was produced as follows.

To 1776 g of water, 412.8 g of ammonium heptamolybdate [$(NH_4)_6Mo_7O_{24}\cdot 4H_2O$], 57.1 g of ammonium metavanadate [$NH_4VO_3$], and 74.8 g of diantimony trioxide [$Sb_2O_3$] were added. While the mixed solution was stirred, the mixed solution was heated at 95° C. for 1 hour to obtain an aqueous raw-material solution (I).

To 405.9 g of a niobium mixed solution ($B_0$), 66.3 g of a hydrogen peroxide solution containing 30 wt % of $H_2O_2$ was added. The solution was stirred and mixed at room temperature for 10 minutes to obtain an aqueous raw-material solution (II).

The obtained aqueous raw-material solution (I) was cooled to 70° C., and 735.7 g of silica sol containing 34.0 wt % of $SiO_2$ was added. Further, 129.3 g of a hydrogen peroxide solution containing 30 wt % of $H_2O_2$ was added, and the obtained solution was continuously stirred at 55° C. for 30 minutes. Next, the aqueous raw-material solution (II), 32.2 g of an aqueous solution of ammonium metatungstate containing 50 wt % of $WO_3$, and a dispersion liquid prepared by dispersing 250 g of powder silica in 3375 g of water were sequentially added to obtain an aqueous mixed solution (III). The aqueous mixed solution (III) was aged at 50° C. for 2 hours 30 minutes after addition of the aqueous raw-material solution (II) to obtain a slurry raw material-prepared solution.

The obtained raw material-prepared solution was fed to the centrifugal spray dryer and dried to obtain a microspherical catalyst precursor. The temperature at the inlet of the dryer was 210° C., and the temperature at the outlet thereof was 120° C.

A calcining tube made of SUS and having a diameter of 3 inches was filled with 200 g of the obtained catalyst precursor. Under a flow of nitrogen gas at 5.0 NL/min, while the calcining tube was rotated, the catalyst precursor was calcined at 680° C. for 2 hours to obtain a composite oxide catalyst.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at reaction temperature of 440° C., a reaction pressure of normal pressure, and a contact time of 2.9 (sec·g/cc) to conduct the ammoxidation reaction. On day 3 after the reaction was started, 0.5 g of tungsten trioxide having an average particle size of 130 µm was added, and 0.5 g of tungsten trioxide having an average particle size of 130 µm was added on day 6. The reaction was conducted for 10 days.

The results of the reaction on day 10 are shown in Table 2.

Example 15

Preparation of Composite Oxide Catalyst

A composite oxide catalyst was prepared by the same method as in Example 2.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of normal pressure, and a contact time of 2.9 (sec·g/cc) to conduct the ammoxidation reaction. On day 3 after the reaction was started, 0.5 g of tungsten trioxide having an average particle size of less than 1 µm was added, and 0.5 g of tungsten trioxide having an average particle size of less than 1 µm was further added on day 6. The reaction was conducted for 10 days.

The results of the reaction on day 10 are shown in Table 2.

Example 16

Preparation of Composite Oxide Catalyst

A composite oxide catalyst was prepared by the same method as in Example 2.

(Ammoxidation Reaction of Propane)

A glass fluidized bed reactor having an inner diameter of 1B was filled with 40 g of the composite oxide catalyst obtained above. A mixed gas in a molar ratio of propane:ammonia:oxygen:helium=1:1:3:18 was fed at a reaction temperature of 440° C., a reaction pressure of normal pressure, and a contact time of 2.9 (sec·g/cc) to conduct the ammoxidation reaction. On day 3 after the reaction was started, 0.5 g of tungsten trioxide having an average particle size of not less than 600 µm was added, and 0.5 g of tungsten trioxide having an average particle size of not less than 600 µm was further added on day 6. The reaction was conducted for 10 days.

The results of the reaction on day 10 are shown in Table 2.

TABLE 1

| | Ammoxidation of propane | | | |
|---|---|---|---|---|
| | Composition of catalyst | | Additive | Method for addition |
| Example 1 | $Mo_1V_{0.2}Nb_{0.1}Sb_{0.2}W_{0.05}O_n$/50 wt %-$SiO_2$ | | WO3 | Before reaction |
| Comparative Example 1 | $Mo_1V_{0.2}Nb_{0.1}Sb_{0.2}W_{0.05}O_n$/50 wt %-$SiO_2$ | | — | — |
| Example 2 | $Mo_1V_{0.21}Nb_{0.1}Sb_{0.22}W_{0.04}O_n$/50 wt %-$SiO_2$ | | WO3 | During reaction (continuous addition) |

TABLE 1-continued

Ammoxidation of propane

| | | | |
|---|---|---|---|
| Example 3 | $Mo_1V0.21Nb0.1Sb0.22W0.04On$/50 wt %-SiO2 | WO3 | During reaction (intermittent addition) |
| Example 4 | $Mo_1V_{0.21}Nb_{0.1}Sb_{0.22}W_{0.04}O_n$/50 wt %-SiO$_2$ | WO3 | During reaction (intermittent addition) |
| Comparative Example 2 | $Mo_1V_{0.21}Nb_{0.1}Sb_{0.22}W_{0.04}O_n$/50 wt %-SiO$_2$ | WO3 | During reaction (intermittent addition) |
| Example 5 | $Mo_1V_{0.21}Nb_{0.1}Sb_{0.22}W_{0.04}O_n$/50 wt %-SiO$_2$ | (NH4)6(H2W12O40)•4H2O | During reaction (intermittent addition) |
| Comparative Example 3 | $Mo_1V_{0.21}Nb_{0.1}Sb_{0.22}W_{0.04}O_n$/50 wt %-SiO$_2$ | — | — |
| Example 6 | $Mo_1V_{0.22}Nb_{0.11}Te_{0.2}O_n$ | WO3 | During reaction (intermittent addition) |
| Comparative Example 4 | $Mo_1V_{0.22}Nb_{0.11}Te_{0.2}O_n$ | — | — |
| Example 7 | $Mo_1V0.2Nb0.1Sb0.23W0.03On$/50 wt %-SiO2 | WO3 | During reaction (intermittent addition) |
| Comparative Example 5 | $Mo_1V0.2Nb0.1Sb0.23W0.03On$/50 wt %-SiO2 | — | — |
| Example 8 | $Mo_1V0.23Nb0.1Sb0.2W0.04On$/50 wt %-SiO2 | WO3 | During reaction (intermittent addition) |
| Comparative Example 6 | $Mo_1V0.23Nb0.1Sb0.2W0.04On$/50 wt %-SiO2 | — | — |
| Example 9 | $Mo_1V_{0.21}Nb_{0.1}Sb_{0.22}W_{0.05}La_{0.005}O_n$/50 wt %-SiO$_2$ | WO3 | During reaction (intermittent addition) |
| Comparative Example 7 | $Mo_1V_{0.21}Nb_{0.1}Sb_{0.22}W_{0.05}La_{0.005}O_n$/50 wt %-SiO$_2$ | — | — |
| Example 10 | $Mo_1V_{0.2}Nb_{0.12}Sb_{0.2}W_{0.03}Ce_{0.005}O_n$/25 wt %-SiO$_2$ | WO3 | During reaction (intermittent addition) |
| Comparative Example 8 | $Mo_1V_{0.2}Nb_{0.12}Sb_{0.2}W_{0.03}Ce_{0.005}O_n$/25 wt %-SiO$_2$ | — | — |
| Example 12 | $Mo_1V_{0.2}Nb_{0.1}Sb_{0.2}W_{0.04}O_n$/65 wt %-SiO$_2$ | WO3 | During reaction (intermittent addition) |
| Comparative Example 10 | $Mo_1V_{0.2}Nb_{0.1}Sb_{0.2}W_{0.04}O_n$/65 wt %-SiO$_2$ | — | — |
| Example 13 | $Mo_1V_{0.22}Nb_{0.11}Sb_{0.2}O_n$/50 wt %-SiO$_2$ | WO3 | During reaction (intermittent addition) |
| Comparative Example 11 | $Mo_1V_{0.22}Nb_{0.11}Sb_{0.2}O_n$/50 wt %-SiO$_2$ | — | — |
| Example 11 | $Mo_1V_{0.21}Nb_{0.1}Sb_{0.22}W_{0.04}O_n$/50 wt %-SiO$_2$ | (NH4)6Mo7O24•4H2O WO3 | During reaction (intermittent addition) |
| Comparative Example 9 | $Mo_1V0.21Nb0.1Sb0.22W0.04On$/50 wt %-SiO2 | (NH4)6Mo7O24•4H2O | During reaction (intermittent addition of only Mo) |

| | W/Mo | Conversion rate [%] | AN selectivity [%] | AN yield [%] | W/Mo | Conversion rate [%] | AN selectivity [%] | AN yield [%] |
|---|---|---|---|---|---|---|---|---|
| | | Day 5 | | | | Day 10 | | |
| Example 1 | 0.0162 | 89.1 | 60.5 | 53.9 | 0.015 | 88.9 | 62.0 | 55.1 |
| Comparative Example 1 | — | 89.4 | 59.4 | 53.1 | — | 89.8 | 59.4 | 53.3 |
| Example 2 | 0.0094 | 89.2 | 60.5 | 54 | 0.0075 | 88.9 | 61.5 | 54.7 |
| Example 3 | 0.0002 | 89.1 | 60.0 | 53.5 | 0.0452 | 88.8 | 61.7 | 54.8 |
| Example 4 | 0.0945 | 88.6 | 60.2 | 53.3 | 0.0911 | 88.5 | 60.5 | 53.5 |
| Comparative Example 2 | 0.2534 | 88.3 | 56.9 | 50.2 | 0.2442 | 88.3 | 55.7 | 49.2 |
| Example 5 | 0.0021 | 88.8 | 60.6 | 53.8 | 0.0017 | 88.5 | 61.7 | 54.6 |
| Comparative Example 3 | — | 89.3 | 59.5 | 53.1 | — | 89.1 | 59.7 | 53.2 |
| Example 6 | 0.0092 | 89.2 | 60.9 | 54.3 | 0.0085 | 88.9 | 62.3 | 55.4 |
| Comparative Example 4 | — | 89.5 | 60.1 | 53.8 | — | 89.6 | 60.2 | 53.9 |
| Example 7 | 0.0155 | 89 | 59.3 | 52.8 | 0.0135 | 88.7 | 60.3 | 53.5 |
| Comparative Example 5 | — | 89.3 | 58.2 | 52 | — | 89.3 | 58.2 | 52 |
| Example 8 | 0.0129 | 89.4 | 58.4 | 52.2 | 0.0114 | 89.1 | 59.6 | 53.1 |
| Comparative Example 6 | — | 89.7 | 57.5 | 51.6 | — | 89.7 | 57.5 | 51.6 |
| Example 9 | 0.0226 | 89.4 | 58.7 | 52.5 | 0.0214 | 89.1 | 59.7 | 53.2 |
| Comparative Example 7 | — | 89.7 | 57.9 | 51.9 | — | 89.9 | 58.0 | 52.1 |
| Example 10 | 0.0082 | 89 | 56.4 | 50.2 | 0.0075 | 88.8 | 57.2 | 50.8 |
| Comparative Example 8 | — | 89.4 | 54.8 | 49 | — | 89.3 | 55.1 | 49.2 |
| Example 12 | 0.0274 | 89.8 | 56.0 | 50.3 | 0.0254 | 89.4 | 56.7 | 50.7 |
| Comparative Example 10 | — | 90.2 | 54.4 | 49.1 | — | 90.4 | 54.5 | 49.3 |
| Example 13 | 0.0216 | 89.6 | 57.1 | 51.2 | 0.0195 | 89.2 | 58.4 | 52.1 |
| Comparative Example 11 | — | 90 | 55.7 | 50.1 | — | 90 | 55.7 | 50.1 |
| | | Day 15 | | | | Day 30 | | |
| Example 11 | 0.0077 | 88.7 | 61.1 | 54.2 | 0.0450 | 89.1 | 61.5 | 54.8 |
| Comparative Example 9 | 0.0077 | 88.7 | 61.1 | 54.2 | 0.0075 | 88.9 | 61.0 | 54.2 |

TABLE 2

| | Composition of catalyst | Additive | Method for addition | Average particle size [μm] | Conversion rate [%] | AN selectivity [%] | AN yield [%] |
|---|---|---|---|---|---|---|---|
| Example 14 | Mo1V0.21Nb0.1Sb0.22W0.03On/50 wt %-SiO2 | WO3 | During reaction (intermittent addition) | 130 | 88.9 | 61.8 | 54.9 |
| Example 15 | $Mo_1V_{0.21}Nb_{0.1}Sb_{0.22}W_{0.05}O_n$/50 wt %-$SiO_2$ | WO3 | During reaction (intermittent addition) | Less than 1 | 88.5 | 60.5 | 53.5 |
| Example 16 | $Mo_1V_{0.21}Nb_{0.1}Sb_{0.22}W_{0.05}O_n$/50 wt %-$SiO_2$ | WO3 | During reaction (intermittent addition) | 600 or more | 87.9 | 58.4 | 51.3 |

The present application is based on Japanese Patent Application (No. 2011-045358) filed to the Japanese Patent Office on Mar. 2, 2011, the contents of which are incorporated herein by reference.

According to the present invention, a method for producing an unsaturated nitrile that can provide a higher selectivity of a target compound in a simpler manner can be provided.

What is claimed is:

1. A method for producing an unsaturated nitrile, comprising:

subjecting propane to a vapor-phase catalytic ammoxidation reaction using a fluidized bed reactor in the presence of a composite oxide catalyst, to produce the unsaturated nitrile, wherein a tungsten compound is added into the fluidized bed reactor during the vapor-phase catalytic ammoxidation reaction, to adjust a molar ratio (W/Mo ratio) of a tungsten contained in the tungsten compound to a molybdenum contained in the composite oxide catalyst that exist within the fluidized bed reactor so that the molar ratio is in a range of 0.0001 to 0.1, and the composite oxide catalyst comprises a composite oxide represented by the following composition formula (1):

$$Mo_1V_aNb_bA_cX_dZ_eO_n \quad (1)$$

wherein component A represents at least one or more elements selected from Te and Sb; component X represents at least one or more elements selected from W, Bi, and Mn; component Z represents at least one or more elements selected from La, Ce, Pr, Yb, Y, Sc, Sr, and Ba; a, b, c, d, e, and n each represent an atomic ratio of the corresponding element per Mo atom; a is in a range of $0.01 \leq a \leq 1$; b is in a range of $0.01 \leq b \leq 1$; c is in a range of $0.01 \leq c \leq 1$; d is in a range of $0 \leq d \leq 1$; e is in a range of $0 \leq e \leq 1$; and n represents a number determined by valences of the component elements; and said method further comprising (1) extracting a mixture of the composite oxide catalyst and the tungsten compound from the fluidized bed reactor during the vapor-phase catalytic ammoxidation reaction; (2) measuring a temporary value of the W/Mo ratio from the mixture obtained by (1); and (3) controlling the W/Mo ratio to fall within the range of 0.0001 to 0.1 based on the temporary value measured in (2).

2. The method for producing the unsaturated nitrile according to claim 1, comprising a step of adding a molybdenum compound into the fluidized bed reactor.

3. The method for producing the unsaturated nitrile according to claim 1 or 2, wherein the composite oxide is carried on 20 to 70% by mass of silica based on a whole amount of the catalyst in terms of $SiO_2$.

* * * * *